United States Patent [19]

Opsal et al.

[11] Patent Number: 5,149,978
[45] Date of Patent: Sep. 22, 1992

[54] APPARATUS FOR MEASURING GRAIN SIZES IN METALIZED LAYERS

[75] Inventors: Jon Opsal, Livermore; Allan Rosencwaig, Danville, both of Calif.

[73] Assignee: Therma-Wave, Inc., Fremont, Calif.

[21] Appl. No.: 624,036

[22] Filed: Dec. 7, 1990

[51] Int. Cl.⁵ .................... G01N 21/86; G01N 15/02
[52] U.S. Cl. ..................................... 250/560; 356/335
[58] Field of Search ............. 250/234, 560, 572, 563, 250/222.2, 235; 356/335, 336, 371, 376

[56] References Cited

U.S. PATENT DOCUMENTS

| | | | |
|---|---|---|---|
| 4,112,309 | 9/1978 | Nakazawa et al. | 250/234 |
| 4,373,817 | 2/1983 | Coates | 250/234 |
| 4,626,101 | 12/1986 | Ogawa et al. | 250/563 |
| 4,707,610 | 11/1987 | Lindow et al. | 250/560 |
| 4,889,998 | 12/1989 | Hayano et al. | 250/563 |
| 4,971,445 | 11/1990 | Sato et al. | 250/572 |
| 5,038,048 | 8/1991 | Maeda et al. | 250/563 |

*Primary Examiner*—David C. Nelms
*Assistant Examiner*—Michael Messinger
*Attorney, Agent, or Firm*—Limbach & Limbach

[57] ABSTRACT

An apparatus (10) is disclosed for evaluating the size of grains in a metalized layer on a semiconductor sample (12). The apparatus includes a laser (20) for generating a probe beam (22). The probe beam is focused to a diameter of about one micron and scanned over the surface of the sample. Variations in the power of the specularly reflected beam are measured. In one aspect of the subject invention, the spacing between minima in the reflectivity signal is used to give a direct measurement of average grain size. The depth of the minima can be used to derive a distribution of the grain size. For very small grains, a statistical evaluation of the reflectivity signal is performed to derive grain size.

16 Claims, 3 Drawing Sheets

ILLUSTRATION OF GRAINS
IN A METALIZED LAYER

APPARATUS FOR MEASURING GRAIN SIZES IN METALIZED LAYERS

TECHNICAL FIELD

The subject apparatus employs optical reflectivity measurements to determine the size of the grains in a metalized layer on a semiconductor sample.

BACKGROUND OF THE INVENTION

In the manufacture of semiconductor integrated circuits, a conductive metal, typically aluminum, is used to create the electrical interconnections between devices formed on the substrate. During fabrication, a layer of aluminum is sputtered onto the upper surface of the semiconductor sample. This process is carefully controlled to maintain uniformity and to produce the desired grain size in the aluminum layer. After the layer is formed, various etching steps are performed to define the proper pathways which define the electrical interconnections.

In the process of developing and thereafter monitoring metalization fabrication procedures, it is desirable to evaluate the size of the metal grains in the layer. Various contact techniques have been developed to determine the size of the grains. Unfortunately, these techniques tend to be slow and destructive so that the sample can not then be used to form a device. In addition these techniques cannot easily measure sub-micron size grains.

There has also been developed at least one noncontact technique which relies on the measurement of optical reflectivity of the sample to determine grain size. In this technique, an unfocused probe beam having a relatively large diameter compared to the size of the grains is directed to the surface of the sample. The power of the specularly reflected probe beam is then monitored. The latter apparatus can detect relatively small angle scattering effects. As the size of the grains in the layer decreases and therefore the number of grain boundaries increase per unit area, the amount of detectable small angle scattering effects are increased. The increase in the small angle scattering effects reduces the amount of power in the specularly reflected beam. Accordingly, information about grain size can be obtained by measuring the variations in the reflected beam power with a lower beam power indicating smaller grain sizes.

While the latter approach provides a noncontact technique it has certain drawbacks principally related to the use of the large diameter probe beam. Measurements using such a large beam will be influenced by field illumination effects. More significantly, the latter approach provides only indirect information and is not measuring actual grain size. In addition, the measurement will only yield an average grain size and will provide no information with respect to the distribution of the size of the grains within the layer.

Accordingly, it is an object of the subject invention to provide an apparatus for measuring the size of the grains in a metalized layer on a semiconductor sample.

It is a further object of the subject invention to provide an apparatus for measuring grain size which relies on optical reflectivity measurements.

It is another object of the subject invention to provide an apparatus which relies on optical reflectivity measurements to directly determine grain size.

It is still another object of the subject invention to provide an apparatus which utilizes a highly focused probe beam to derive information about grain size while avoiding adverse field illumination effects.

It is still a further object of the subject invention to provide an apparatus which can determine the distribution of the sizes of the grains in a metalized layer.

SUMMARY OF THE INVENTION

In accordance with these and many other objects the subject apparatus is configured to evaluate the size of the grains in a metalized layer on a semiconductor sample. The apparatus includes a laser for generating a probe beam of radiation. The probe beam is focused onto the surface of the sample to a diameter on the order of one micron using a high powered microscope objective. The probe beam is scanned relative to the surface of the sample. The power of the specularly reflected probe is monitored as a function of the position of the beam on the surface of the sample.

In a first aspect of the subject invention, a direct measurement of the grain size can be made for grains which are larger than about two microns. This result can be achieved because the grain boundaries produce measurable large angle scattering effects in the highly focused beam. Accordingly, as the beam is scanned over the grain boundaries, sharp drops in the reflectivity signal will occur. The average spacing between the minima of the reflectivity signal corresponds to the average size of the grains on the sample.

The extent to which the minima fall can also be correlated to grain size. It has been found that the boundaries associated with larger grains will scatter more light and therefore the drop in the reflectivity signal will be more pronounced. By evaluating the minima over a large sample, a plot of the distribution of the grain sizes in the metalized layer can be generated.

For grain sizes below about two microns, the minima associated with grain boundaries can not be adequately distinguished from minima caused by other surface effects so that an actual measurement of the spacing between boundaries can not be performed. However, it has been found that a statistical evaluation of the variations in the measured reflectivity signal can be used to derive the average size of the grains.

In the preferred embodiment, the statistical evaluation for smaller grain sizes includes a calculation of the standard deviation of the reflectivity signal. The standard deviation will be proportional to grain size. The actual average grain size is determined through calibration techniques.

Further objects and advantages of the subject invention will become apparent from the following detailed description taken in conjunction with the following drawings in which:

DETAILED DESCRIPTION OF THE PREFERRED EMBODIMENT

Figure 1:
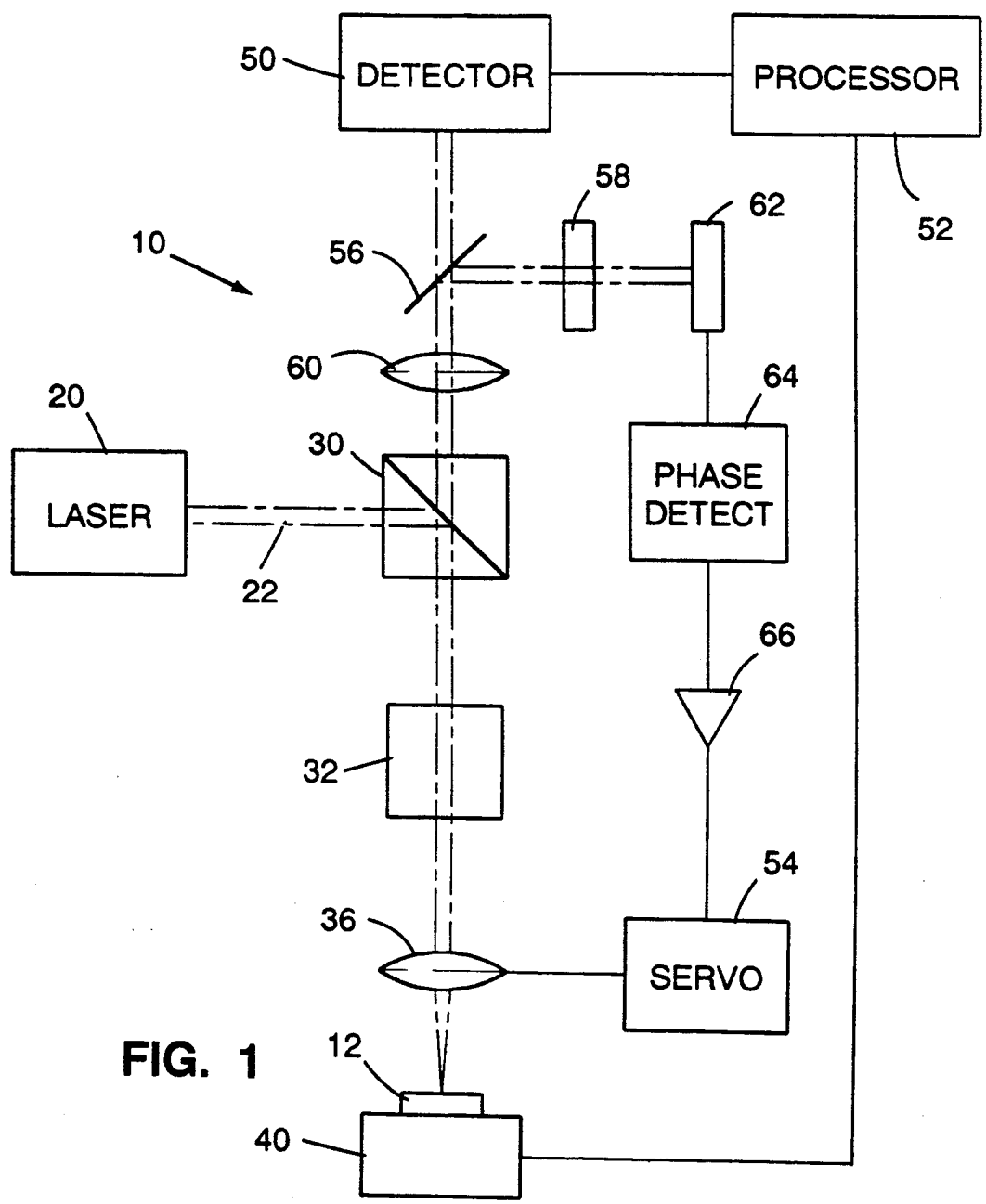
FIG. 1 is a schematic diagram of an apparatus formed in accordance with the subject invention.

Referring to FIG. 1, there is illustrated an apparatus 10 for evaluating the sizes of grains in a metalized layer on a semiconductor sample 12. Typically, these layers are formed from aluminum or aluminum compounds such as aluminum-copper. An enlarged view of the surface of such a sample 12 illustrating the grains 60 is provided in FIG. 2. It should be noted that the size of the grains typically vary and are arranged in a random fashion.

The subject apparatus includes a laser 20 for generating a probe beam 22. In the preferred embodiment, laser 20 is a linearly polarized HeNe laser generating an output beam 22 of 633 nm having a 5 mW power.

The probe beam 22 is directed downwardly by a polarizing beam splitter 30 through a quarter wave plate 32. The beam then passes through lens 36 and onto the surface of the sample 12 with 3 mW of incident power. In the preferred embodiment, lens 36 is a powerful microscope objective having a high numerical aperture (NA). The NA of the lens should be at least 0.5 and is preferably on the order of 0.95. This diffraction limited optical arrangement is arranged to produce spot sizes on the sample having a diameter on the order of one micron. In the preferred embodiment, the spot size is set to 0.8 microns. The lens is spaced from the surface of the sample an amount substantially equal to its focal length. This position is maintained using an autofocus mechanism discussed in greater detail below.

A stage 40 is provided to support the sample 12 and for scanning the sample with respect to the probe beam. This stage provides scanning in two orthogonal directions as well as for rotation of the sample.

The reflected probe beam will pass back up through lens 36 and quarter wave plate 32. The two passes through the quarter waveplate 32 function to rotate the polarization of the beam a full 90 degrees so that when the beam reaches splitter 30 it will pass therethrough to fall on photodetector 50. Photodetector 50 can be a standard element for generating a voltage proportional to the light energy striking the surface. Since optical reflectivity of the sample is to be measured, the total power of the reflected beam should be detected. Accordingly, the geometry should be arranged such that the reflected probe beam substantially underfills the surface of the detector.

The output of the photodetector 50 is supplied to processor 52. Processor 52 is also connected to the stage 40 so that the measurements can be correlated to the position of the beam on the surface of the sample.

As noted above, in the preferred embodiment, lens 36 is maintained a distance from the surface of the sample an amount substantially equal to the focal length of the lens. In the case of the preferred 0.95 NA lens, this distance is about 300 microns. This distance is maintained to within 500 angstroms through the use of an autofocus mechanism.

The autofocus mechanism includes a servo motor 54 for varying the vertical position of the lens 36. The servo is driven by an analog detection loop which determines if the lens 36 is properly focusing the probe beam. As seen in FIG. 1, a partially reflective mirror 56 picks off a small portion of the reflected probe beam and directs it to a chopper wheel 58. A lens 60 is positioned in the path of the reflected probe beam such that the chopper wheel 58 is in the focal plane of the lens. The light passing the chopper wheel 58 is imaged on a split cell photodetector 62. If the lens 36 is out of focus, there will be a phase difference in the light striking the two sides of the split cell 62 which is measured by a phase detector 64. The phase difference is used as an input to an amplifier 66 which in turn drives the servo 54. This approach to autofocusing is known as automated Foucault testing.

Having discussed the elements of the subject apparatus its operation will now be described. In order to determine grain size, the processor causes the stage to move so that the probe beam 22 scans the surface of the sample. The measurements can be taken on the fly and processor will record the reflectivity signal as a function of the position of the probe beam on the surface of the sample.

Figure 2:
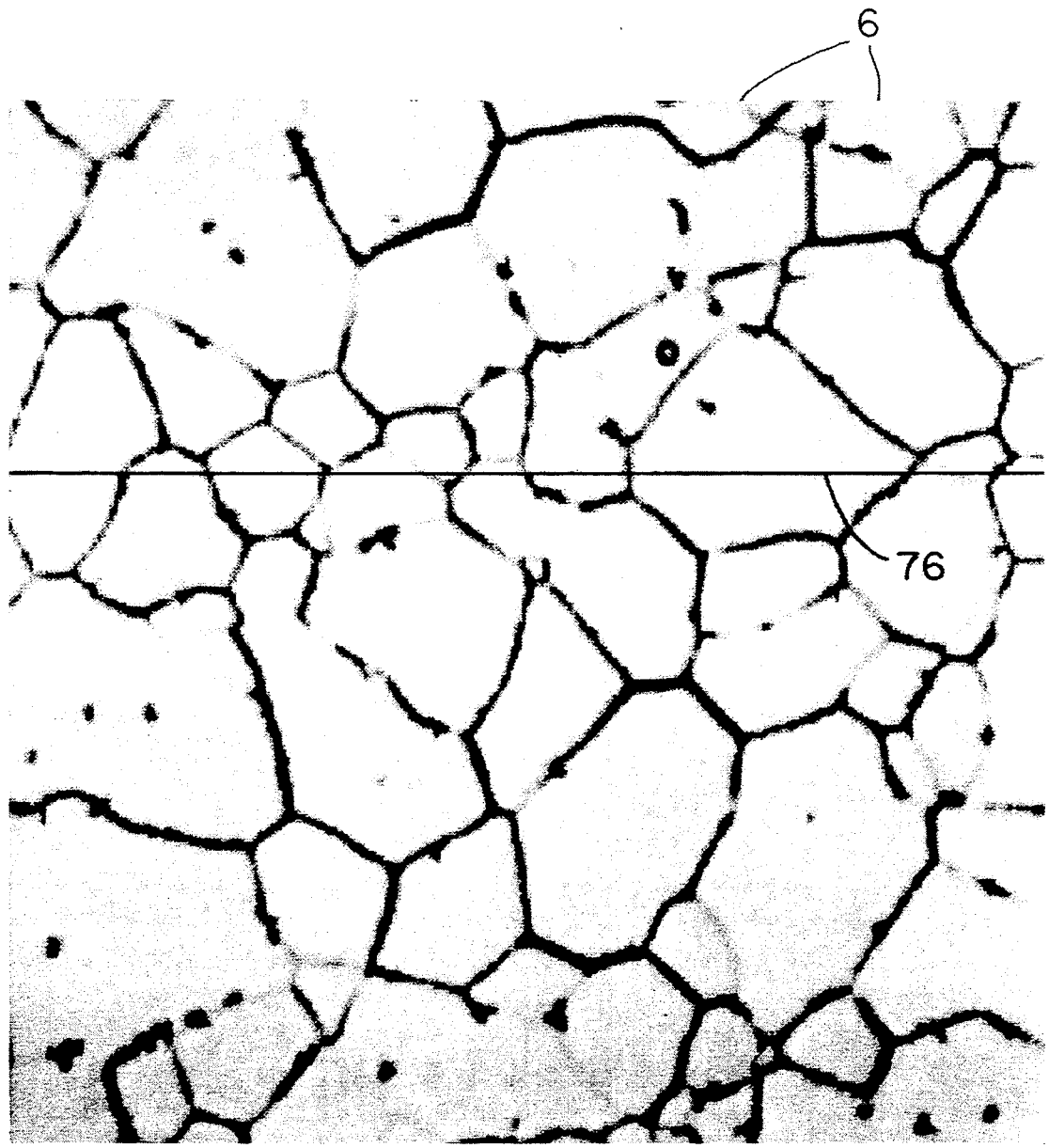
FIG. 2 is an illustration of the grains in a metalized layer.
Figure 3:
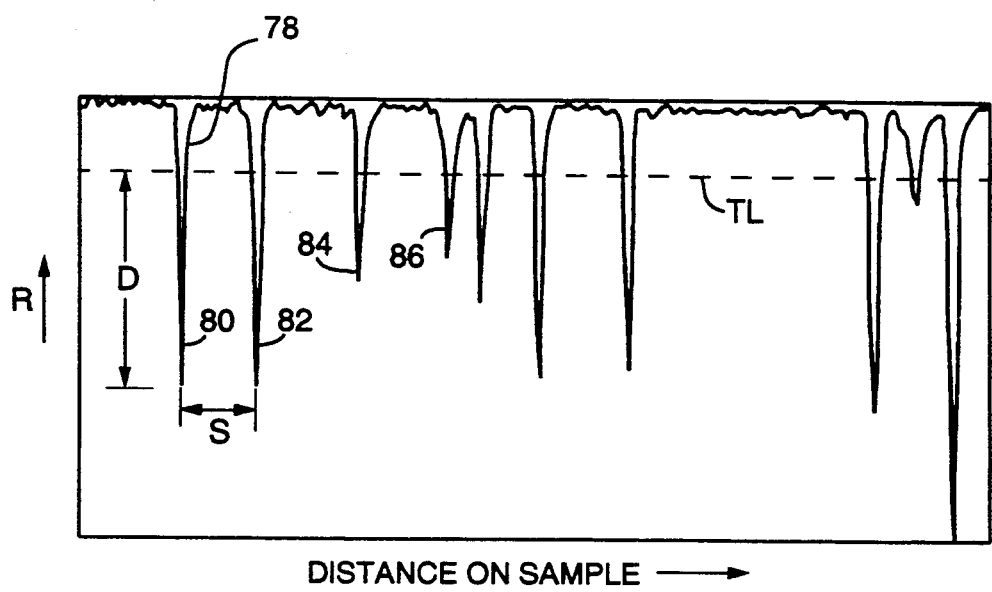
FIG. 3 is a plot of a reflectivity signal which would be generated by the apparatus of the subject invention when measuring grains having a size greater than about two microns.

FIG. 3 illustrates an example of the type of reflectivity signal 78 recorded by the processor as the probe beam is scanned across a sample (along line 76 in FIG. 2). As can be seen, there are a plurality of minima 80, 82, 84, and 86. These minima correspond to grain boundaries where a much higher percentage of the probe beam light is scattered such that the light reaching the detector 50 is sharply reduced.

The sharp and distinct minima 80 through 86 shown in FIG. 3 are of the type that would be observed where the grain sizes are about two microns in diameter or greater. Under these circumstances, the average grain size can be calculated directly from the spacing S between the minima. It should be noted that the spacing between adjacent minima can vary significantly even if the size of the grains are fairly constant over the scanned sample. The variation occurs because the grains do not have a uniform diameter and are randomly arranged as shown in FIG. 2. Thus, the individual spacing between any two minima would not provide an accurate measure of grain size. However, if enough measurements are taken, the average spacing can be used to calculate the average size of the grains. If the scan covers at least one hundred grain boundaries, an average grain size calculation should be accurate to within one percent.

In operation, the processor will first record the data generated by the detector. The location of each minima which falls below a predetermined threshold level (TL) would be identified. The threshold level would be set to distinguish between the grain boundaries and other factor that effect the signal to a smaller extent, such as surface irregularities. The spacing S between each identified minima is then calculated. This spacing is based on the actual distance the probe beam traveled on the surface of the sample. An average is then calculated as set forth below where n is the number of identified minima.

$$\text{Average grain size} = \text{sum of spacings}/n-1 \tag{1}$$

The signal generated by the processor 50 can also be used to evaluate the distribution of grain sizes in the tested region. It has been found that the amount of scattering at the grain boundaries and therefore the depth of the minima, is also related to the size of the grain. More particularly, as the grain size increases, the boundaries tend to become more distinct and scattering increases such that the depth of the minima detected increase.

Figure 4:
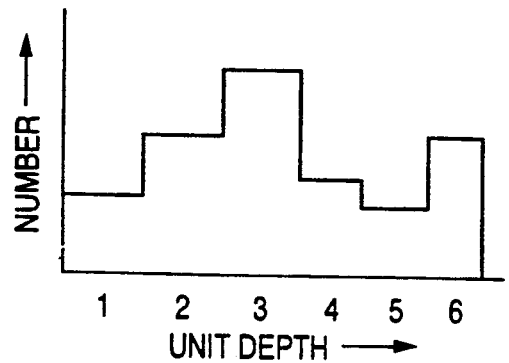
FIG. 4 is a plot of the distribution of grain sizes in a metalized film which can be generated with the apparatus of the subject invention.

In order to generate a plot of the grain size distribution, the processor must determine the depth (D) of each of the minima. This depth can be normalized against the average reflectivity. Then the identified minima can be plotted in relation to their depth (D) through a pixel binning procedure as illustrated in FIG. 4. The X-axis in FIG. 4 represents the normalized level measurement. The Y-axis represents the number of minima which have that normalized level measurement. Each of the detected minima are used as a single pixel input to build the histogram. This procedure will produce a histogram that correlates with the actual distribution of grain sizes. If the sample size includes at least one hundred grains, an accurate picture of the distribution of grain size can be generated.

In order to scale the normalized measurements on the X-axis to actual grain sizes, a calibration procedure is necessary. Correlation is performed with a plurality of test wafers. More particularly, a plurality of test wafers having various known grain size distributions are measured and the results stored in a table in the processor. The scale of the distribution can then be determined with reference to the table.

Figure 5:
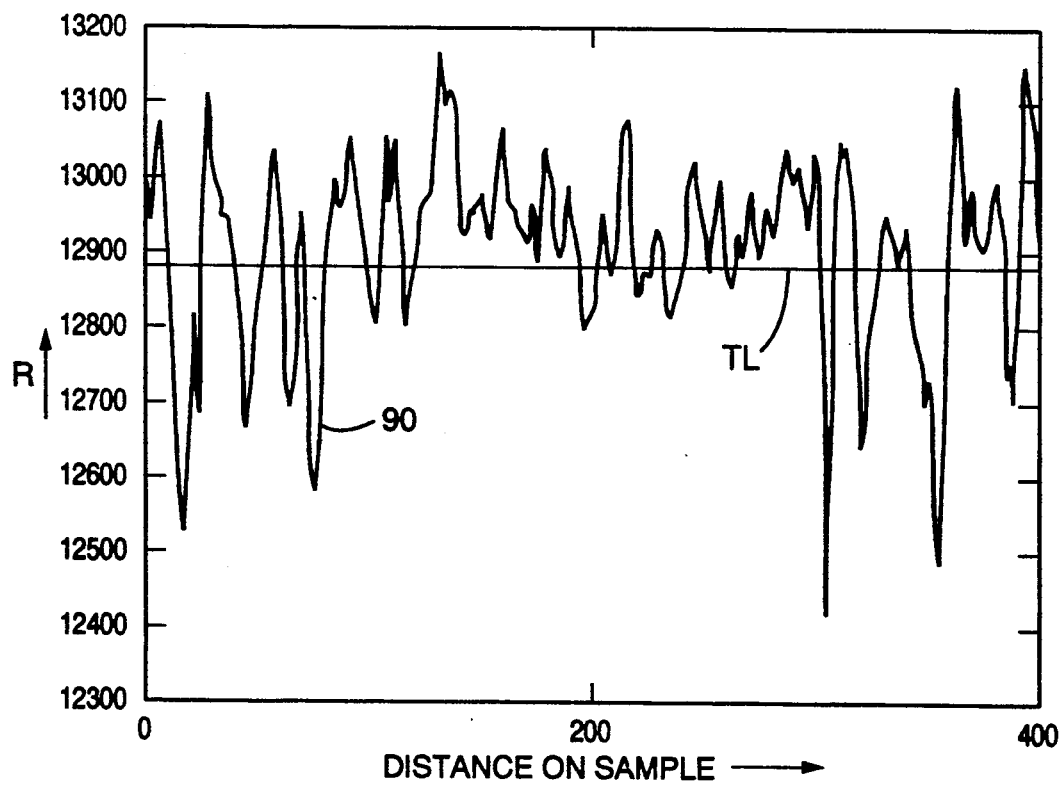
FIG. 5 is a plot of a reflectivity signal which would be generated by the apparatus of the subject invention when measuring grains having a size less than about two microns.

The type of signal 90 which can be expected when the size of the grains falls below two microns is shown in FIG. 5. In this range, the extent of the change in the reflectivity signal due to the grain boundaries is reduced and therefore less distinguishable from the variations in the reflectivity signal caused by changes in surface topography. Therefore, it is much more difficult to identify the minima associated solely with grain boundaries. Nonetheless, the predominant variation in the reflectivity signal is still produced from the presence of grain boundaries. Therefore, as long as sufficient data is taken, the average grain size can still be determined through a statistical analysis. It has been found that if at least one hundred boundaries are detected, grain sizes as small as 0.25 microns can be measured.

In accordance with the subject invention, the preferred statistical analysis includes the computation of the standard deviation of the reflectivity signal. The standard deviation is proportional to the average grain size. The standard deviation (sigma) is calculated in the following manner where R is the reflectivity signal and n is the number of measurements falling below a threshold level (TL).

$$\text{sigma} = \sqrt{<R^2_{RMS}> - (R_{AVERAGE})^2} \quad (2)$$

where $$<R^2_{RMS}> = \frac{1}{N} \sum_{n=1}^{N} R_n \quad (3)$$

and $$<R_{AVERAGE}> = \frac{1}{N} \sum_{n=1}^{N} R_n \quad (4)$$

In order to correlate the standard deviation to grain size, the system is calibrated with test wafers in a manner similar to that discussed above. More particularly, a plurality of test wafers having various known grain sizes are measured and the standard deviations stored along with the associated grain size in a table in the processor. The grain size of the tested sample can then be determined with reference to the table.

It should be noted that this statistical approach can be used to determine the grain size of grains larger than two microns. However, it is believed that the previously described approach is preferred for larger grain sizes since it is more direct and does not require calibration. In addition, the procedure described above for generating a plot representative of grain size distribution can be utilized even when grain size falls below two microns in diameter.

In summary, there has been disclosed an apparatus 10 for evaluating the size of grains in a metalized layer on a semiconductor sample 12. The apparatus includes a laser 20 for generating a probe beam 22. The probe beam is scanned over the surface of the sample and variations in the power of the specularly reflected beam are measured. In one aspect of the subject invention, the spacing between minima in the reflectivity signal is used to give a direct measurement of average grain size. The depth of the minima can be used to derive a distribution of the grain size. For very small grains, a statistical evaluation of the reflectivity signal is performed to derive grain size.

While the subject invention has been described with reference to a preferred embodiment, various changes and modifications could be made therein, by one skilled in the art, without varying from the scope and spirit of the subject invention as defined by the appended claims.

We claim:

1. An apparatus for evaluating grain sizes on the surface of the sample, wherein the grains have irregular shapes, said apparatus comprising:
   means for generating a probe beam;
   means for scanning the probe beam with respect to the surface of the sample an amount sufficient to cross a plurality of grain boundaries;
   means for measuring the power of the reflected probe beam as a function of the position of the probe beam on the surface of the sample; and
   processor means for evaluating the sizes of the grains on the sample surface based on the probe beam power measurements, said processor means functioning to determine the average distance on the sample between locations where the power measurement drops below a predetermined threshold level to derive the average grain size.

2. An apparatus as recited in claim 1 further including a means for focusing the probe beam on the surface of the sample to a diameter on the order of one micron.

3. An apparatus for evaluating the distribution of grain sizes on the surface of the sample, wherein the grains have irregular shapes comprising:
   means for generating a probe beam;
   means for scanning the probe beam with respect to the surface of the sample an amount sufficient to cross a plurality of grain boundaries;
   means for measuring the power of the reflected probe beam as a function of the position of the probe beam on the surface of the sample; and
   processor means for evaluating the distribution of grain size on the sample surface based on a determination of the number of times the minima of the probe beam power measurements fall below a predetermined threshold level in combination with a determination of the depth of these minima.

4. An apparatus as recited in claim 3 wherein the processor means derives the distribution of grain sizes by analyzing the distribution of depth of the minima.

5. An apparatus as recited in claim 3 further including a means for focusing the probe beam on the surface of the sample to a diameter on the order of one micron.

6. An apparatus for evaluating grain sizes on the surface of the sample, wherein the grains have irregular shapes, said apparatus comprising:
 means for generating a probe beam;
 means for focusing the probe beam onto the surface of the sample to diameter on the order of one micron;
 means for scanning the probe beam with respect to the surface of the sample an amount sufficient to cross a plurality of grain boundaries;
 means for measuring the power of the reflected probe beam as a function of the position of the probe beam on the surface of the sample; and
 processor means for evaluating the average size of the grains on the sample surface based on a statistical analysis of the variations in the probe beam power measurements.

7. An apparatus as recited in claim 6 wherein said processor means functions to calculate the standard deviation of the probe beam power measurements.

8. An apparatus as recited in claim 6 wherein the variations in the probe beam power measurements are compared with variations measured on test pieces having a known grain size to determine the grain size of the sample.

9. A method for evaluating grain sizes on the surface of the sample, wherein the grains have irregular shapes, said method comprising the steps of:
 generating a probe beam;
 scanning the probe beam with respect to the surface of the sample an amount sufficient to cross a plurality of grain boundaries;
 measuring the power of the reflected probe beam as a function of the position of the probe beam on the surface of the sample; and
 evaluating the sizes of the grains on the sample surface based on the probe beam power measurements by determining the average distance on the sample between locations where the power measurement drops below a predetermined threshold level to derive the average grain size.

10. A method as recited in claim 9 further including the step of focusing the probe beam on the surface of the sample to a diameter on the order of one micron.

11. A method for evaluating the distribution of grain sizes on the surface of the sample, wherein the grains have irregular shapes, said method comprising the steps of:
 generating a probe beam;
 scanning the probe beam with respect to the surface of the sample an amount sufficient to cross a plurality of grain boundaries;
 measuring the power of the reflected probe beam as a function of the position of the probe beam on the surface of the sample; and
 evaluating the distribution of grain size on the sample surface based on a determination of the number of times the minima of the probe beam power measurements fall below a predetermined threshold level in combination with a determination of the depth of these minima.

12. A method as recited in claim 11 wherein the distribution of grain sizes is derived by analyzing the distribution of depth of the minima.

13. A method as recited in claim 11 further including the step of focusing the probe beam on the surface of the sample to a diameter on the order of one micron.

14. A method for evaluating grain sizes on the surface of the sample, wherein the grains have irregular shapes, said method comprising:
 generating a probe beam;
 focusing the probe beam onto the surface of the sample to diameter on the order of one micron;
 scanning the probe beam with respect to the surface of the sample an amount sufficient to cross a plurality of grain boundaries;
 measuring the power of the reflected probe beam as a function of the position of the probe beam on the surface of the sample; and
 evaluating the average size of the grains on the sample surface based on a statistical analysis of the variations in the probe beam power measurements.

15. A method as recited in claim 14 wherein said evaluation step includes the step of calculating the standard deviation of the probe beam power measurements.

16. A method as recited in claim 14 wherein the variations in the probe beam power measurements are compared with variations measured on test pieces having a known grain size to determine the grain size of the sample.

* * * * *